United States Patent [19]

Ambur et al.

[11] Patent Number: 5,497,649

[45] Date of Patent: Mar. 12, 1996

[54] INTERNALLY DAMPED, SELF-ARRESTING VERTICAL DROP-WEIGHT IMPACT TEST APPARATUS

[75] Inventors: Damodar R. Ambur; Chunchu B. Prasad, both of Yorktown; William A. Waters, Jr., Virginia Beach; Robert W. Stockum, Poquoson; Manfred A. Walter, Newport News, all of Va.

[73] Assignee: The United States of America as represented by the Administrator of the National Aeronautics and Space Administration, Washington, D.C.

[21] Appl. No.: 414,253

[22] Filed: Mar. 31, 1995

Related U.S. Application Data

[62] Division of Ser. No. 250,141, May 20, 1994, Pat. No. 5,457,984.

[51] Int. Cl.$^6$ .................................................. G01N 3/00
[52] U.S. Cl. ........................................ 73/12.06; 73/12.09
[58] Field of Search ................................ 73/12.01, 12.06, 73/12.09, 12.13

[56] References Cited

U.S. PATENT DOCUMENTS 3,453,862  7/1969  Elliott et al. ............................ 73/12.13
4,313,337  2/1982  Myint ..................................... 73/12.13
4,649,735  3/1987  Pihaja .................................... 73/12.13

*Primary Examiner*—Richard Chilcot
*Assistant Examiner*—R. Biegel
*Attorney, Agent, or Firm*—Robin W. Edwards

[57] ABSTRACT

A vertical dropped-weight impact test machine has a dropped-weight barrel vertically supported on upper and lower support brackets. The dropped-weight barrel is chambered to receive a dropped-weight assembly having a latch pin at its upper end, a damping unit in the middle, and a tup at its lower end. The tup is adapted for gathering data during impact testing. The latch pin releasably engages a latch pin coupling assembly. The latch pin coupling assembly is attached to a winch via a halyard for raising and lowering the dropped-weight assembly. The lower end of the dropped-weight barrel is provided with a bounce-back arresting mechanism which is activated by the descending passage of the dropped-weight assembly. After striking the specimen, the dropped-weight assembly rebounds vertically and is caught by the bounce-back arresting mechanism. The damping unit of the dropped-weight assembly serves to dissipate energy from the rebounding dropped-weight assembly and prevents the dropped-weight assembly from rebounding from the self-arresting mechanism.

3 Claims, 4 Drawing Sheets

FIG. 2
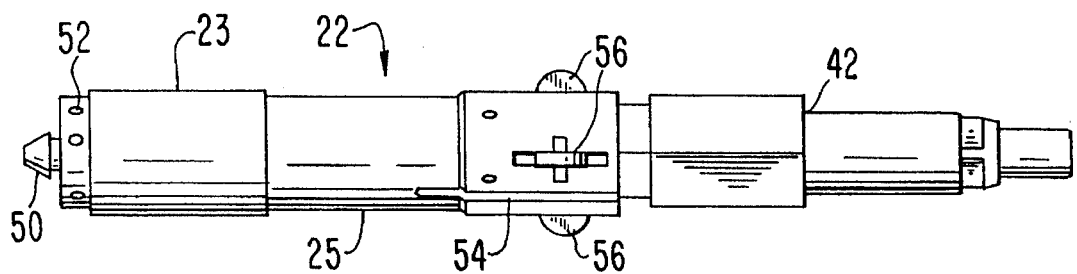
FIG. 3
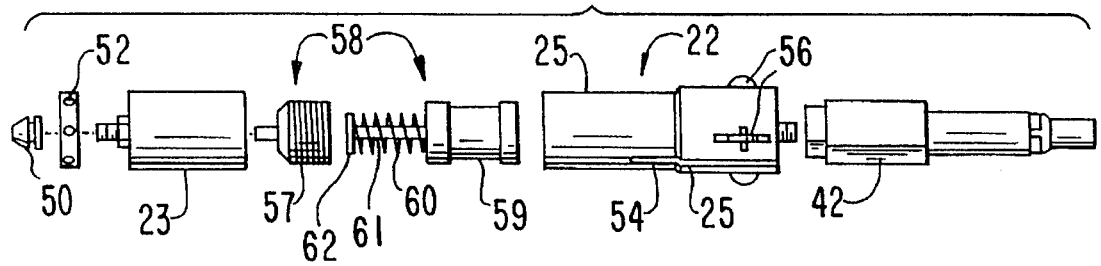
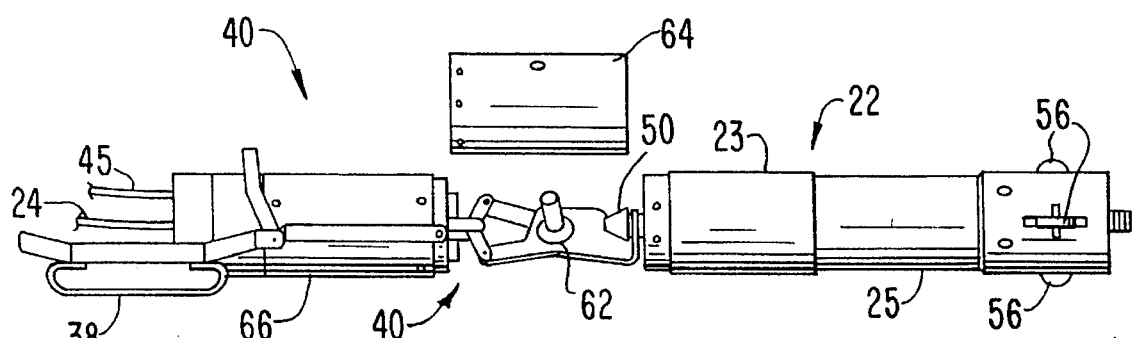
FIG. 4

INTERNALLY DAMPED, SELF-ARRESTING VERTICAL DROP-WEIGHT IMPACT TEST APPARATUS

This is a divisional of application Ser. No. 08/250,141 filed on May 20, 1994 now U.S. Pat. No. 5,457,984, issued Oct. 12, 1995.

ORIGIN OF THE INVENTION

The invention described herein was jointly made by a NASA employee and by a contractor employee in the perfotmance of work under NAS1-19000 and is subject to the provisions of Section 305 of the National Aeronautics and Apace Act of 1958, as amended, Public Law 85-568 (72 Stat. 435; 42 USC 2457), and contractor employees in the performance of work under NASA Contracts NAS1-19235 and NAS1-13317 and is subject to the provisions of 35 U.S.C. 202. In accordance with 35 U.S.C. 202, the contractors elected not to retain title.

BACKGROUND OF THE INVENTION

1. Field of the Invention

This invention relates in general to an impact test apparatus, and specifically to dropped-weight testing assembly for impact testing of composite materials and structures by vertically dropping a weight from a predetermined height.

2. Description of the Related Art

The use of composite materials for structural applications is increasing due to cost and weight advantages provided by composites. For example, composite materials find applications as structural parts of aircrafts. However, test data have shown that the compression strength of certain composite structures can be significantly reduced by low speed impact damage, e.g., tools dropped by maintenance and assembly personnel. Such low speed impact damage is often undetectable by visual inspection. The sensitivity of the compression strength of composite structures to low speed impact damage has led to the development of more damage tolerant materials and to the development of special damage tolerance design criteria for composite structures.

In order to accurately determine the effect of low speed impacts on composite structures and materials, dropped-weight testing apparatus and procedures have been developed. These apparatus and procedures call for the dropping of a weight, of given size and material, onto a specimen from a given height to generate a certain impact response. In general, investigators have used either a free-fall dropped-weight or a pendulum apparatus to impact the specimen. The present invention relates to a vertical free-fall dropped-weight testing apparatus.

Currently, two types of dropped-weight machines are used by researchers for impacting test specimens. One is a sophisticated dropped-weight system for screening materials in a manual or automated manner for damage tolerance characteristics. In such systems, the weight is typically guided by two or four guide bars and hoisted by a motor operated cable system. Thereafter, the weight is released and descends to impact the test specimen. To prevent multiple impacts, the dropped-weight is arrested by means of a hydraulic or pneumatically actuated system after rebounding from the test specimen. Such machines are typically very expensive and can only test small specimens.

The second type of dropped-weight test apparatus is a basic machine where the weight is moved manually up a frame to a predetermined height and released by pulling a locking-pin mechanism. After impact, the weight is manually caught as it rebounds from the test specimen. Not only is such an operating procedure unsafe, but the impact location cannot be accurately controlled, making for wide discrepancies in the accuracy of acquired test data.

U.S. Pat. No. 3,106,834 to Parstorfer discloses a high acceleration impact shock testing apparatus which comprises a tester carriage slidably constrained for movement between parallel guide members. The tester carriage includes a specimen carrier and an impact member. A slidably disposed rebound stop member also carried by the carriage, is laterally deflected upon impact to frictionally engage the stop member with the guide members thereby terminating movement of the carriage at the peak of its rebound from the impact. Shock, strain or impact registering transducers may be carried by the specimen carrier for registering suitable outputs indicating shock, strain, impact, etc. As the specimen travels with the impact member, the size of the specimen is limited.

U.S. Pat. No. 3,103,116 to Kohli discloses a shock testing machine having a brake mechanism for preventing multiple rebounds of a dropped-weight assembly. The brake mechanism comprises a pneumatic brake which is actuated by a control circuit to prevent relative movement between the weight assembly and guide rods.

U.S. Pat. No. 3,209,580 to Colby discloses a device for preventing multiple rebounds of an impacting mass of a free-falling shock testing machine. The device for preventing multiple rebounds of the impacting mass comprises an air cylinder including a reciprocative piston.

U.S. Pat. No. 4,505,362 to Layotte et al. discloses a device for avoiding multiple bounces of a vertically falling mass after a first impact. The device comprises at least one deformable element secured to a guide and a control is adapted to press the deformable element against a lateral wall of the mass after its bounce and to secure the latter in position.

U.S. Pat. No. 2,590,486 to Aubert discloses a scleroscope having a clutching mechanism for stopping a test plunger at a maximum height of rebound. A movable hammer plunger of a magnetic material is slidably positioned in a guide passage. The hammer plunger is dropped from a predetermined height onto a surface to be tested. A magnetic wedge in the frame acts as a clutching or braking mechanism to stop downward movement of the plunger after it has reached its maximum rebound height.

U.S. Pat. No. 2,496,420 to Stern discloses a drop weight test apparatus having two parallel vertical guides, a top plate at the top of the guides, a bottom plate, a weight slidably mounted on the guides, a supporting plate slidably mounted on the guides and bearing a hydraulic velocity reducer. A specimen is mounted for testing beneath the hydraulic velocity reducer by applying a compressive force to it. Between the specimen and the top plate is mounted a piezoelectric strain gage. The weight is raised to a desired height by means of a line. The line is then released so that weight falls, striking the top of the hydraulic velocity reducer. The impact is transmitted through the velocity reducer to the test specimen and the strain gage. The shock or concussion of the impact is absorbed by a resilient layer.

U.S. Pat. No. 2,475,614 to Hoppmann, II, et al. discloses an apparatus for electrically measuring strain applied in testing strength of materials by impact testing. The testing apparatus comprises a tower extending upwardly from an anvil to a predetermined height. A specimen assembly comprises a hammer or tup and a weight attached to respective opposite sides of a specimen of a material being tested, the specimen being enclosed inside a spacer. The specimen is dropped from a predetermined height in the tower and is guided by rails of the tower toward the anvil with the weight in advance and the hammer trailing. The weight is contoured to enter an aperture of the anvil without interference and the hammer is contoured to extend laterally and overhang the sides of the aperture, whereby it strikes the anvil. A weight bar couples the weight to the specimen. A series of strain gages are fastened on the sides of the bar.

U.S. Pat. No. 161,737 to Beardslee discloses a testing apparatus comprising an iron hammer mounted between two vertical rods, an anvil and a hoisting/release assembly. The hammer is raised by the hoisting assembly. A specimen is then placed on the anvil and the hammer is released to strike the specimen.

U.S. Pat. No. 3,998,090 to Wislocki discloses a dropped hammer soil compactor including a limit mechanism used to control the distance of the hammer drop. The limit mechanism includes upper and lower limit valves. The upper limit valve is fixed, but the lower limit valve is vertically adjustable.

U.S. Pat. No. 4,640,120 to Garritano et al. discloses an impact testing apparatus including a weighted dart which is dropped from a prescribed height to penetrate a test specimen. A force transducer is located at the tip of the dart for providing impact force information as the tip penetrates the test specimen.

U.S. Pat. No. 1,901,460 to Lewis discloses testing apparatus adapted to test the strength of the materials by subjecting the material to a number of impacts imposed by a weight dropped from predetermined heights. A mechanical inertial switch on the impacting weight is used to prevent multiple strikes. Upon striking the test specimen, the switch is propelled downward allowing lifting lugs to engage a central guide rod. The lifting rod and latch pins form a ratchet mechanism which allows motion of the weight upward, but restrains any motion downward.

SUMMARY OF THE INVENTION

Accordingly, it is an object of the present invention to provide an impact test apparatus able to cause a single accurate impact by a dropped-weight on a wide variety of test specimens.

It is another object of the present invention to provide an impact test apparatus adapted to gently secure the dropped-weight on its first rebound prior to reimpacting upon the test specimen, thereby reducing strain on the testing apparatus.

It is a further object of the present invention to provide an economical dropped-weight impact test apparatus able to accurately deliver a single impact upon test specimens of various sizes.

These and other objects are accomplished by an internally damped, self-arresting vertical dropped-weight impact test apparatus which comprises an elongated barrel defining a descent path, support means for holding the barrel vertically over a specimen to be tested, a dropped-weight assembly adapted to move vertically through the barrel along the descent path, the dropped-weight assembly having an internal damping structure, and a tup for measuring the force of the impact, at least one jaw member adapted to engage the dropped weight assembly to arrest its movement upon rebound, the jaw member being engageable through a slot in the elongated barrel, and means for causing the jaw member to engage the dropped-weight assembly after the dropped-weight assembly has rebounded subsequent to impacting the specimen.

BRIEF DESCRIPTION OF THE DRAWINGS

The present invention and the objects achieved by it will be understood from the description herein, with reference to the accompanying drawings, in which:

FIG. 2 is a lateral view of an embodiment of a dropped-weight assembly for use in the present invention.

FIG. 3 is an exploded view of the dropped-weight assembly for use in the present invention.

FIG. 4 is a lateral view of the clasp mechanism for use in the present invention.

DETAILED DESCRIPTION OF THE PREFERRED EMBODIMENTS

Figure 1:
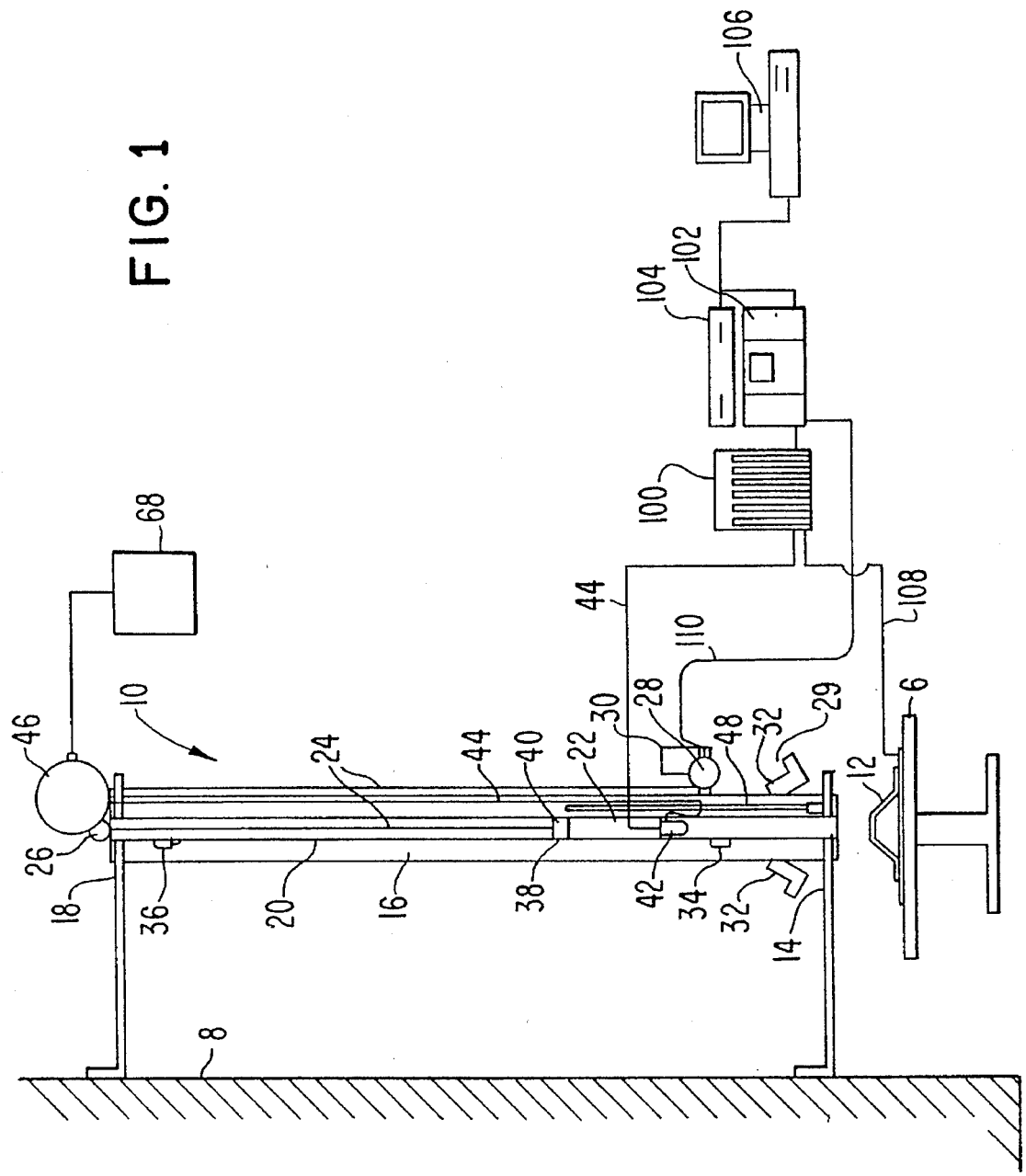
FIG. 1 is a lateral sectional view of an embodiment of the present invention.

FIG. 1 shows a lateral sectional view of an internally damped, self-arresting dropped-weight test apparatus for impact testing of various structures according to a first preferred embodiment of the invention. FIG. 1 is simplified to show only those elements necessary for understanding the invention. The vertical dropped-weight impact test apparatus, shown generally at 10, is rigidly supported from a support structure 8 above a tilt table 6 holding a specimen 12. Various conventional means may be used to rigidly secure the vertical dropped-weight impact test apparatus 10 to the support structure. However, in the preferred embodiment the vertical dropped-weight impact test apparatus 10 is held in place by a lower support bracket 14 and an upper support bracket 18 which are bolted to the support structure 8. An elongated tube is used as a dropped-weight barrel 16. Although a variety of cross-sectional configurations and materials may be used for the tube, a square seamless metallic tube is particularly well suited for use as a dropped-weight barrel. A dropped-weight assembly 22 is guided by the dropped-weight barrel 16 towards specimen 12. A bounce-back arresting mechanism 29 engages the rebounding dropped weight assembly after the specimen has been impacted once, thereby preventing further impacts of the specimen 12.

FIG. 2 shows the dropped-weight assembly 22 which comprises an instrumented tup 42 at the lower end of the dropped-weight assembly 22, a guide cylinder 25 connected at one end to the instrumented tup 42, and an upper weighted area which includes a weight cylinder 23 which is connected to the other end of the guide cylinder 25. The materials and dimensions of the weight cylinder 23 are selected to produce the desired weight to impact the specimen 12. Variations in material and dimensions for the weight cylinder can be made in order to adjust the total weight of the dropped-weight assembly 22 as it impacts different specimens 12.

The upper end of the dropped-weight assembly is provided with a latch pin 50 for engagement with a latch pin coupling assembly 40 as shown in FIG. 1. Guide pins 52 operate in conjunction with guide wheels 56 to insure that the dropped-weight assembly 22 maintains its orientation within the dropped-weight barrel 16. Slots 54 are provided in the guide cylinder 25 of the dropped-weight assembly 22 for engagement with the bounce-back arresting mechanism 29 shown in FIG. 1 in the engaged position.

FIG. 3 shows an exploded view of the dropped-weight assembly 22. The guide cylinder 25 of the dropped-weight assembly 22 has a cavity which receives a damping unit 58. The damping unit 58 is further comprised of a cylinder 59 with an internal cavity filled with a gel and a piston rod 61 to create a dashpot. A helical spring 60 is securely positioned on the piston rod 61 in a preloaded condition by means of an end plate 62. The end cap 57 serves as an adapter between the damping unit 58 and the weight cylinder 23. The damping unit 58 acts to absorb shocks on the dropped-weight assembly 22 resulting from its activation of the arresting mechanism 29 and when it is caught by the arresting jaws 32 on rebound from the test specimen 12. The damping unit 58 enables the bounce-back arresting mechanism 29 to experience smaller shock forces when the dropped-weight assembly 22 is engaged. The damping action also prevents the dropped-weight assembly 22 from rebounding against the self-arresting mechanism 29.

The instrumented tup 42, refering to FIG. 1, is a metallic impactor which preferably incorporates a load cell adapted for measuring contact forces in the range from 0 to 10,000 lbs. For example, suitable 0 to 5,000 lb. and 0 to 10,000 lb. force transducers with model numbers 8496-1 and 8496-2, respectively, can be obtained from Dynatup, Inc., Santa Barbara, Calif. The tup 42 is connected to a tup cable 44 for collection of data during the testing operation. The tup cable 44 extends through slot 20 in the dropped-weight barrel 16 and is connected to a signal conditioning amplifier 100. A latch pin coupling assembly 40 is releasably attached to dropped-weight assembly 22 through halyard 24. A drive motor 30 operates a halyard winch 28 to raise and lower the latch pin coupling assembly 40 via pulley 26.

FIG. 4 shows a lateral view of the preferred embodiment of the latch pin coupling assembly 40 engaging the dropped-weight assembly 22. An enclosure 64 holds a scissors-like clasp mechanism 62. The clasp mechanism 62 is actuable by a solenoid unit 66. An electrical cable 45 is attached at one end to the solenoid unit 66. This cable 45 runs through the take-up spool 46, see FIG. 1, which keeps the cable under constant tension to prevent it from entangling with other components of the apparatus when the dropped-weight assembly 22 is raised or lowered. The cable 45 is connected at its other end to control box 68. Solenoid unit 66 is operable to open clasp mechanism 62 thereby releasing the retaining latch pin 50 of dropped-weight assembly 22. In the preferred embodiment, the clasp mechanism 62 is opened by the solenoid in order to release the dropped-weight assembly 22 to impact a specimen 12. When it is desired to engage the latch pin 50 in the clasping mechanism 62, the clasping operation is accomplished mechanically by physically positioning the latch pin 50 in the clasp mechanism 62.

Referring once again to FIG. 1, the dropped-weight barrel 16 is provided with an adjustable upper limit switch 36 that determines the maximum height of operation for the dropped-weight assembly 22. Similarly, dropped-weight barrel 16 is provided with an adjustable lower limit switch 34 that determines the minimum height of operation of the dropped weight assembly 22. The limit switches act to shut off power to the drive motor 30 and the solenoid unit 66, thereby ensuring that the dropped-weight assembly 22 is not inadvertantly released. The latch pin coupling assembly 40 is provided with a limit switch contact 38 to activate the functions provided by the limit switches.

Figure 5:
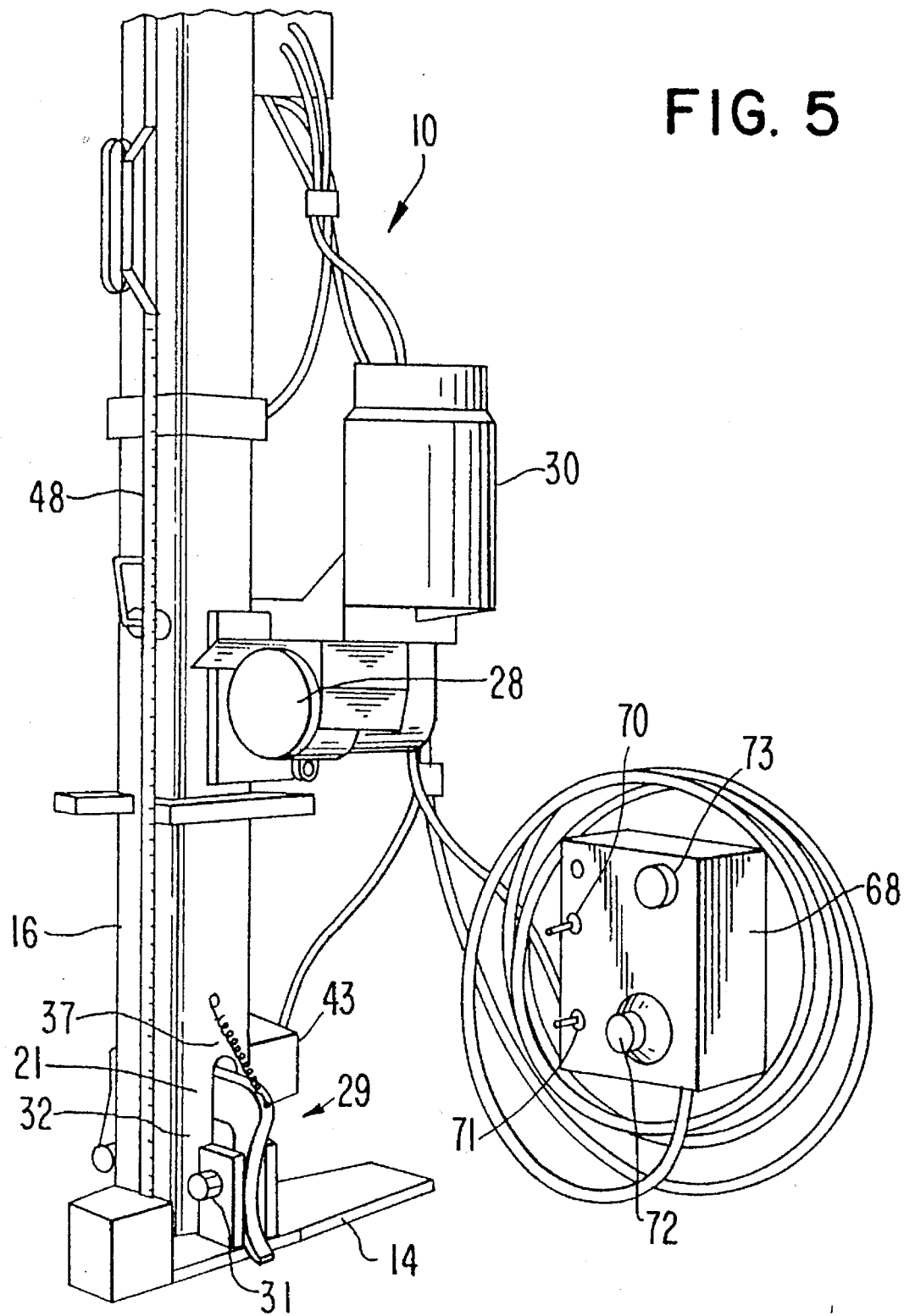
FIG. 5 is a perspective view of the present invention.

FIG. 5 shows an isometric view of the vertical dropped-weight impact test apparatus 10 including the bounce-back arrestor mechanism 29 in its cocked position. The bounce-back arresting mechanism 29 comprises a pair of substantially Z-shaped arresting jaws 32. The arresting jaws 32 are pivotally connected to the dropped-weight barrel 16 via a pair of pivot pins 31. A pair of opposed arrestor slots 21 are provided in the dropped weight barrel 16 to receive the broad heads of arresting jaws 32. A pair of springs 37 bias the arresting jaws 32 towards slots 21.

Figure 6:
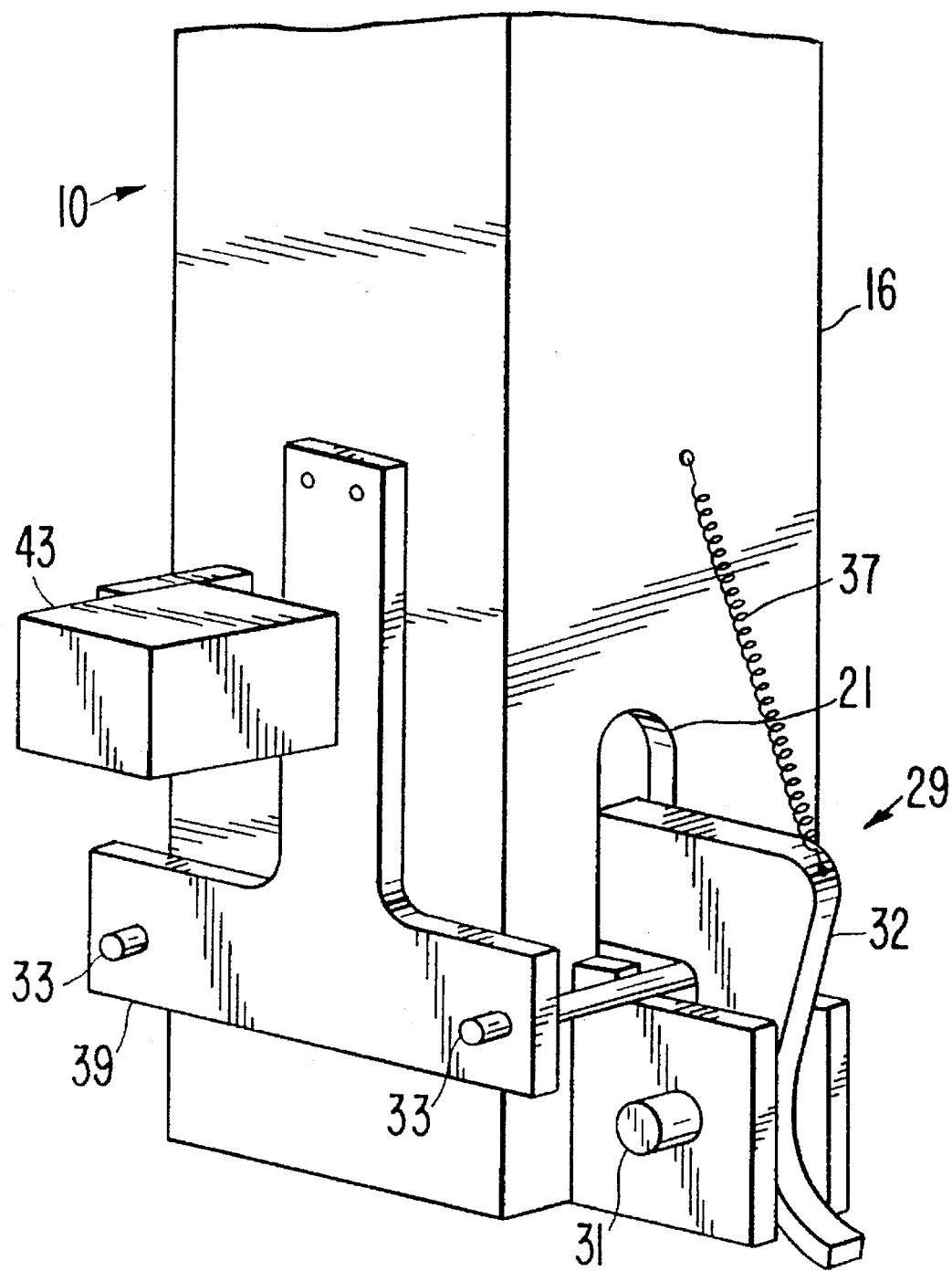
FIG. 6 is a perspective view of the lower portion of the present invention illustrating the bounce-back arrestor mechanism.

FIG. 6 shows an isometric view of the lower portion of the vertical dropped-weight impact test apparatus illustrating the bounce-back arrestor mechanism 29. A pair of spring-loaded restraining pins 33 are connected to a flexible plate 39 which is attached to the outside of the dropped-weight barrel 16 such that the restraining pins 33 are biased towards the arresting jaws 32. A cam (not shown) is in contact with and disposed behind the flexible plate 39 and extends through the dropped-weight barrel 16 such that it minimally intrudes into the descent path of the dropped-weight assembly 22. When the dropped-weight assembly 22 descends, it pushes the cam outward causing the restraining pins 33 to disengage from the arresting jaws 32. In the cocked position, the spring-loaded restraining pins 33 prevent the arresting jaws 32 from entering the dropped weight barrel 16 until the descending dropped-weight assembly 22 disengages the pins 33. When the spring-loaded pins disengage the arresting jaws 32, the arresting jaws 32 are biased toward slots 21 by the helical springs 37. A trigger switch 43 is in contact with the flexible plate 39, and movement of the restraining pins 33 results in a corresponding movement of the flexible plate to activate the trigger switch 43. The trigger switch 43 controls power to switch 73, as shown in FIG. 5. Thus, the switch 73 that releases the clasp mechanism 62 is rendered inoperable unless the restraining pins are engaged with the cocked arresting jaws 32. The trigger switch 43 also includes an electrical circuit that provides a triggering voltage to the data recording unit when the restraining pins 33 are disengaged as a result of the dropped weight assembly 22 passing the cam.

Refering again to FIG. 5, an isometric view of the vertical dropped-weight impact test apparatus 10 coupled to a control apparatus 68 is shown. The control apparatus 68 is powered through switch 70. The control apparatus 68 communicates with the drive motor 30, and latch pin coupling assembly 40, see FIG. 4. A dropped-weight positioning switch 71 on the control apparatus 68 activates a motor 30 which causes winch 28 to raise and lower the latch pin coupling assembly 40. The speed with which the assembly can be raised or lowered can be selected by setting the position of dial 72. A switch 73 is provided on the control apparatus 68 for activating the solenoid unit 66 on clasp mechanism 62 to release the dropped-weight assembly 22.

In operation, the height of the latch pin coupling assembly 40 is indicated by a measuring device 48. Upon raising the dropped-weight assembly to the desired height, the arresting jaws 32 are placed in their cocked position to engage the restraining pins with the arresting jaws 32 and to make the switch 73 operable. The solenoid unit 66 in the latch pin coupling assembly 40 is then activated through switch 73 to release the clasp mechanism 62. Dropped-weight assembly 22 then drops vertically through the dropped-weight barrel 16 towards the specimen 12. When the dropped-weight assembly 22 passes by the self-arresting mechanism 29 it trips the cam to move the flexible plate 39 and the restraining pins and thus release the arresting jaws 32. The arresting jaws 32 are forced toward the dropped-weight barrel 16, through arrestor slots 21, by springs 37. After the dropped-weight assembly 22 rebounds from specimen 12, the slots 54 on the dropped-weight assembly 22 are engaged by the arresting jaws 32. The damping unit 58, in conjunction with the spring 60, acts to absorb most of the shock from the dropped-weight assembly 22 when it trips the cam and engages with the arresting jaws 32 and prevents it from rebounding from the now engaged self-arresting mechanism 29. Thereafter, the vertical dropped-weight impacting test apparatus 10 is reset by lowering the latch pin coupling assembly 40 onto latch pin 50 of dropped-weight assembly 22. After the clasp mechanism 62 has engaged latch pin 50, halyard winch 28 is activated to raise the dropped-weight assembly 22. Thereafter, the self-arresting mechanism 29 is once again cocked to prepare the dropped-weight impact testing apparatus 10 for another impact test.

Looking once again at FIG. 1, a data collection system is shown therein. Three data leads: a specimen data cable 108, a trigger data cable 110, and tup cable 44 are used to control and monitor all data output of the vertical dropped-weight impact test apparatus 10. A signal conditioning amplifier 100 receives data from the tup cable 44 and the specimen data cable 108. The signal conditioning amplifier 100 amplifies the signals which are then recorded on a digital storage oscilloscope 102. A data storage system 104 and a computer 106 operate to store and process the data from the specimen data cable 108 and tup cable 44. Trigger data cable 110 feeds to the data storage oscilloscope 102.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. A method of testing the effect of an impact of a weight dropped through a barrel onto a specimen comprising:

aligning the barrel to accurately deliver a single impact from the weight upon the specimen;

supporting the barrel above the specimen;

dropping the weight upon the specimen;

impacting the weight upon the specimen;

mechanically catching the weight on a first rebound from the specimen; and damping resulting shock of the weight on the means for catching the weight resulting from catching the weight of the first rebound, wherein damping is accomplished by a means internal to the weight.

2. A method of testing the effect of impact, as recited in claim 1, wherein the step of mechanically catching the weight comprises:

pivotally connecting a pair of substantially Z-shaped jaws to the barrel such that the jaws are biased into the path of the weight;

holding the jaws away from the path of the weight;

releasing the jaws after the weight has passed the jaws;

catching the weight with the jaws on the first rebound from the specimen; and damping the force of the impact of the weight upon the jaws by a means internal to the weight.

3. A method of testing the effect of an impact of a weight dropped through a barrel onto a specimen comprising:

aligning the barrel to accurately deliver a single impact from the weight upon the specimen;

supporting the barrel above the specimen;

dropping the weight upon the specimen;

impacting the weight upon the specimen;

catching the weight on a first rebound from the specimen; and damping resulting shock of the weight on the means for catching the weight resulting from catching the weight of the first rebound, wherein damping is accomplished by a means internal to the weight.

* * * * *